United States Patent
Spencer

(10) Patent No.: US 7,099,078 B2
(45) Date of Patent: Aug. 29, 2006

(54) BORESCOPE WITH SIMULTANEOUS VIDEO AND DIRECT VIEWING

(75) Inventor: Lee Spencer, Southend-on-Sea (GB)

(73) Assignee: KEYMED (Medical & Industrial) Limited, Essex (GB)

( * ) Notice: Subject to any disclaimer, the term of this patent is extended or adjusted under 35 U.S.C. 154(b) by 0 days.

(21) Appl. No.: 10/487,042

(22) PCT Filed: May 2, 2003

(86) PCT No.: PCT/GB03/01891

§ 371 (c)(1),
(2), (4) Date: Feb. 18, 2004

(87) PCT Pub. No.: WO03/107068

PCT Pub. Date: Dec. 24, 2003

(65) Prior Publication Data

US 2004/0189799 A1    Sep. 30, 2004

(30) Foreign Application Priority Data

Jun. 18, 2002  (GB) .................................. 0213982.2

(51) Int. Cl.
*A61B 1/04*    (2006.01)
(52) U.S. Cl. ........................ 359/434; 600/112; 600/167
(58) Field of Classification Search ................ 359/434, 359/435; 600/101, 112, 130, 163, 167, 172, 600/174
See application file for complete search history.

(56) References Cited

U.S. PATENT DOCUMENTS

| | | | |
|---|---|---|---|
| 4,565,423 A * | 1/1986 | Ueda ........................... | 359/503 |
| 4,737,622 A * | 4/1988 | Shishido et al. ............ | 250/204 |
| 4,905,082 A | 2/1990 | Nishigaki et al. | |
| 5,808,813 A * | 9/1998 | Lucey et al. ................. | 359/694 |
| 6,333,812 B1 * | 12/2001 | Rose et al. .................. | 359/367 |
| 6,549,333 B1 * | 4/2003 | Nakatate et al. ............ | 359/368 |
| 2001/0012053 A1 * | 8/2001 | Nakamura .................... | 348/45 |
| 2003/0097044 A1 * | 5/2003 | Rovegno ..................... | 600/170 |

FOREIGN PATENT DOCUMENTS

| | | |
|---|---|---|
| DE | 3928421 | 5/1991 |
| EP | 0 054 127 | 6/1982 |
| EP | 0 712 600 | 5/1996 |
| JP | 3 0060628 | 3/1991 |

(Continued)

*Primary Examiner*—Mark A. Robinson
*Assistant Examiner*—Mark Consilvio
(74) *Attorney, Agent, or Firm*—Smith, Gambrell & Russell, LLP

(57) ABSTRACT

An assembly is described for connection to a borescope to simultaneously provide a virtual image for direct viewing by an observer and a video image for viewing on a display. The assembly (10) comprises a body (12) with a distal end for connection to an insertion tube of a borescope and a proximal end providing an eye piece into which an observer may look. The body contains a relay lens (16) and an ocular lens (18). A beam splitter (28) is mounted in the optical path between the relay lens (16) and the ocular lens (18) and diverts a proportion of light received from the relay lens (16) to an image-to-video conversion device (30) mounted laterally to the optical path. The ocular lens (18), beam splitting device (28) and the image-to-video conversion device (30) are all located in a common mounting (38) which can be translated in a direction parallel to the optical path to allow for focussing.

14 Claims, 2 Drawing Sheets

FOREIGN PATENT DOCUMENTS

| | | |
|---|---|---|
| WO | WO 91/03201 | 3/1991 |
| WO | WO 97/27798 | 8/1997 |
| WO | WO 01/50947 | 7/2001 |

* cited by examiner

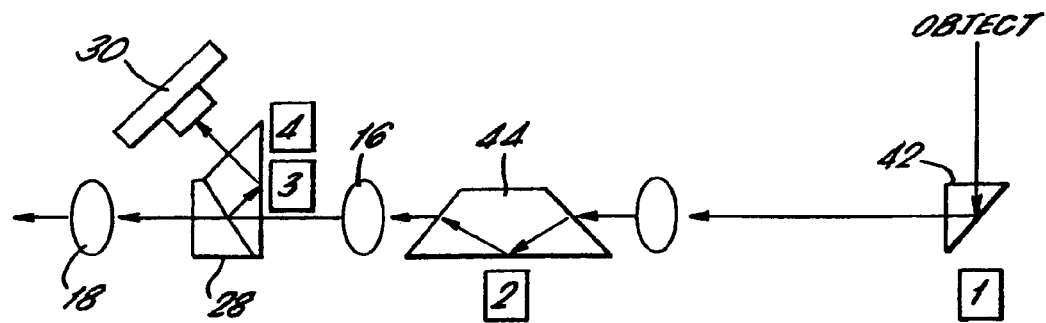
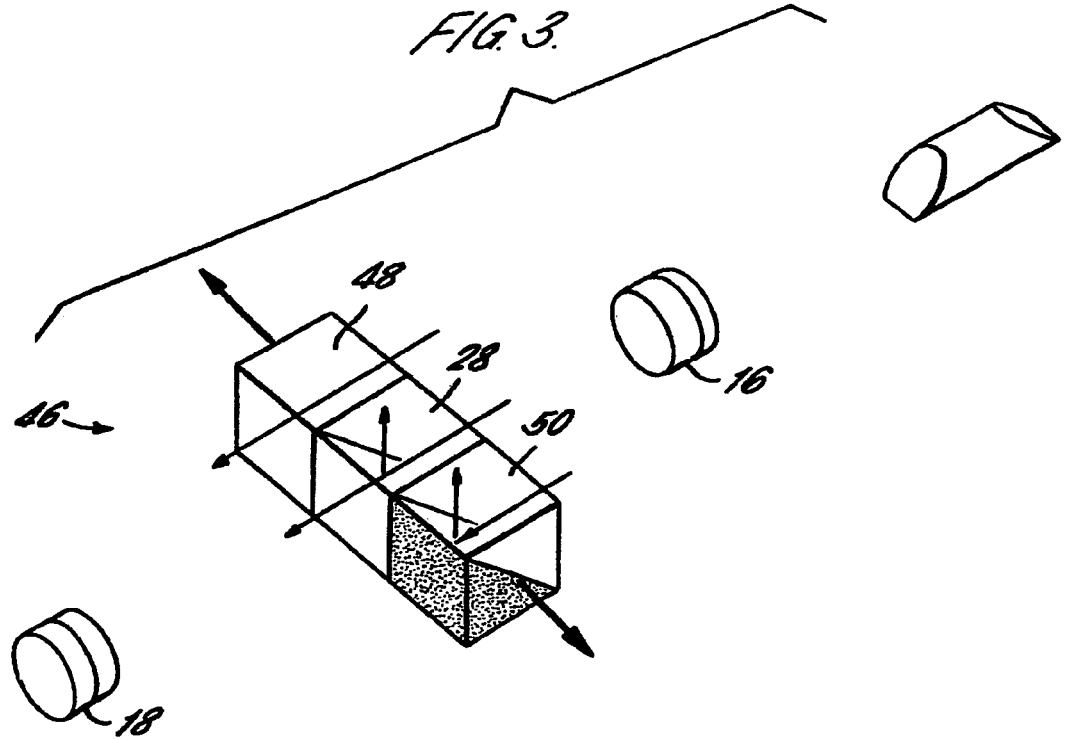

BORESCOPE WITH SIMULTANEOUS VIDEO AND DIRECT VIEWING

The present invention relates to a borescope which simultaneously provides a virtual image for direct viewing by an observer and a video image viewing on a display.

As used herein, the term borescope refers to any form of optical instrument used to form an image of an object at an inaccessible or inconvenient location and to transmit the image to another more convenient location for viewing. Such instruments are often referred to by other names such as endoscope, fibrescope, videoscope etc.

These instruments usually include an insertion tube, which may be rigid or flexible, with a housing at the proximal end. An objective lens system at the distal end of the insertion tube forms an image of an object. This is transmitted to the proximal end for viewing. Borescopes generally fall into two categories, that is those including visual systems and those having video systems.

A visual system comprises three optical sections. First, an objective lens system is provided at the distal end of the insertion tube. This may include a prism arrangement to change the direction of view. The objective lens system forms an image of the object. Secondly, a relay system is provided which transfers the image from the distal end of the insertion tube to the proximal end. This may be a train of lenses such as standard lenses, rod lenses or gradient index (GRIN) lenses, or a bundle of optical fibres. Thirdly, an ocular lens system is provided in housing at the proximal end of the scope. This takes the real image from the end of the relay system and forms a virtual image for an observer's eye to view at a comfortable distance away, typically one meter, equivalent to −1 dioptre.

The benefits of a visual system include a high resolution image, a high dynamic range, i.e. the ability to see detail in both bright and dark areas of the image at the same time, a high brightness image, portability, lower cost and high temperature resistance of the insertion tube.

Video systems also comprise an objective lens system as in a visual scope, but in this case the image is formed on an image-to-video converter, such as a CCD (charge coupled device). The CCD turns the optical image into an electrical signal which can be passed by cable to the proximal end of the scope. An image processor is provided to process the video signal into a form that can be viewed on a display, such as a monitor screen.

The benefits of a video system include the ability to record and manipulate images and to display images on a screen and hence to have a large magnification of the object under inspection and the ability for multiple viewers to see the image at the same time. It also leads to a reduction in eye strain and a possible reduction in size of the housing of the scope, to allow the scope to be used in smaller spaces.

It is possible to attach a still or video camera to the eyepiece of a visual borescope to convert the image to a video signal. However, doing this removes the ability to examine a visual image at the same time. This also increases complexity and cost, and adapters are required to connect the camera to the scope. The additional size of the camera and adapter can also limit the usefulness of the scope in confined spaces.

The present invention provides an assembly for a borescope, comprising a body having a distal end for connection to an insertion tube and a proximal end providing an eyepiece into which an observer may look, the body containing a relay lens for receiving light from a relay system in the insertion tube, an ocular lens for creating a virtual image for viewing by an observer and a beam splitter device mounted in the optical path between the relay lens and the ocular lens and operable to divert a proportion of light received from the relay lens to an image-to-video conversion device mounted laterally to the optical path, and wherein the ocular lens, beam splitting device and image-to-video conversion device are located in a common mounting translatable in a direction parallel to the optical path to allow for focussing.

In this way, the advantages of visual and video scopes can be achieved with a single, compact unit and focussing can be achieved simultaneously for the visible image path and for the video image path for different working ranges of the scope.

Preferably, a collar is rotatably mounted on the body and coupled to the common mounting such that rotation of the collar causes translation of the mounting in a direction parallel to the opt+

In a preferred embodiment, the beam splitter device is a beam splitter cube operable to divert a proportion of light at substantially 90° to the optical path.

Conveniently, the beam splitter device is operable to divert approximately 50% of light received to the image-to-video conversion device.

Advantageously, the beam Splitter device is adjustable to alter the proportion of light diverted to the image-to-video conversion device.

In one embodiment, the beam splitter device comprises a first element operable to transmit all light received from the relay lens along the optical path to the ocular lens, a second element operable to transmit a first proportion of light along the optical path and to divert a second proportion of light to the image-to-video conversion device and a third element operable to divert all the light received to the image-to-video diversion device, wherein the first, second and third elements are selectively moveable to position one element at a time in the optical path.

In this way, depending upon the application, the user can select whether simultaneous visual and video images are obtained or whether to optimise any one form of image.

Conveniently, the image-to-video conversion device comprises CCD board camera which preferably comprises a full digital signal processing means, for compactness.

To accommodate use with borescopes that include a prism at the distal end of the insertion tube for lateral viewing, the image-to-video conversion device may be programmable to allow for correction of image inversion.

Alternatively, the beam splitter device may be configured to ensure an image received by the image-to-video conversion device has been reflected an even number of times.

Additionally, an inversion correction device may be mounted in the body proximal to the ocular lens, to ensure correction of the image viewed directly by an observer.

To provide a clear defined edge to the image, a field mask is mounted in the optical path at the location of the final real image, between the last relay lens and the beam splitter device.

The present invention also provides a borescope comprising an insertion tube connected to an assembly of the type described above.

The invention will now be described in detail, by way of example only, with reference to the accompanying drawings in which:

FIG. 2 is a schematic side view of an arrangement of lenses and prisms for use in a second embodiment of the invention; and FIG. 3 is a schematic perspective view of an arrangement of lenses and prisms for use in a third embodiment of the present invention.

Figure 1:
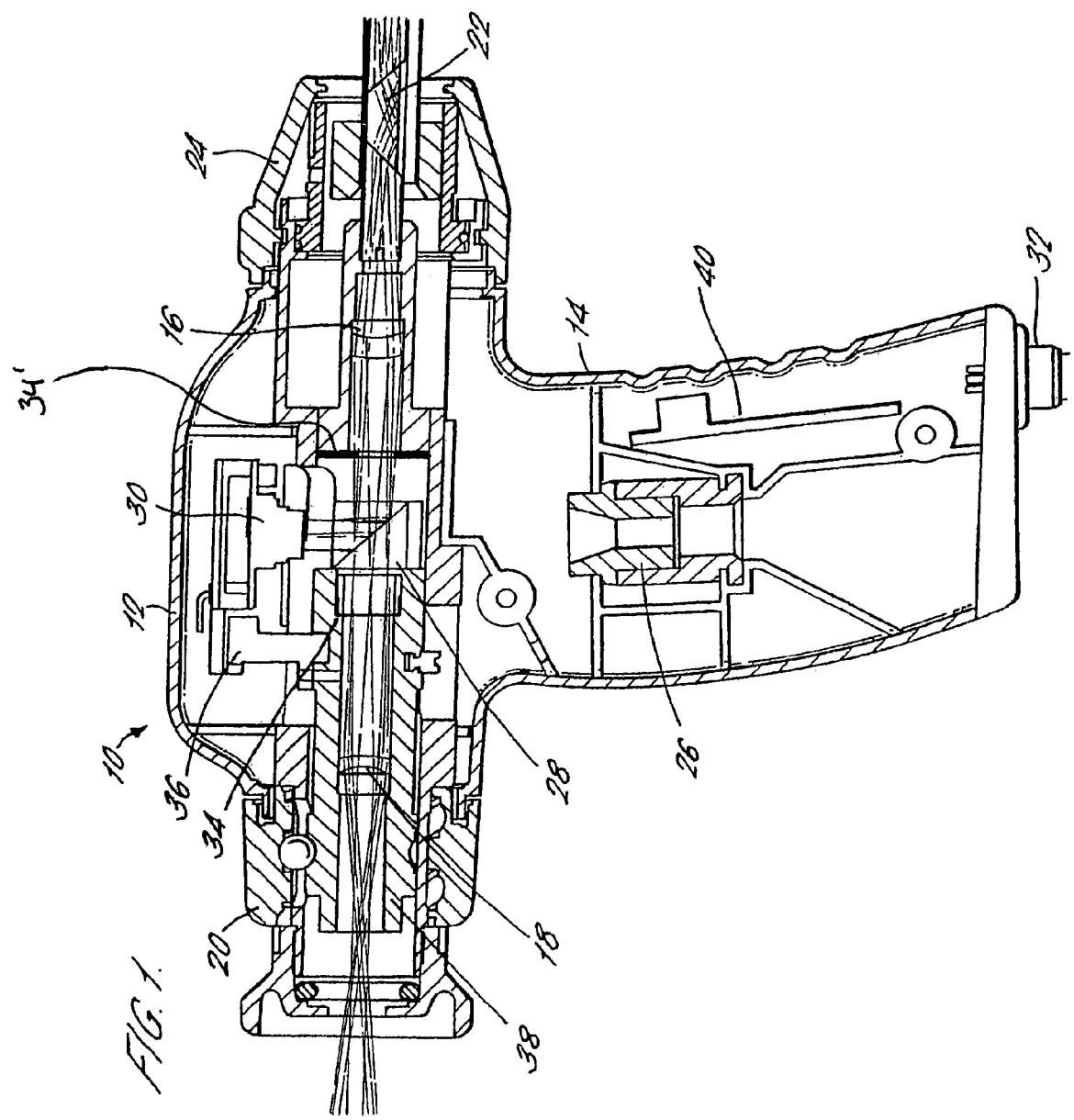
FIG. 1 is a schematic cross-sectional view of the housing of a borescope in accordance with a first embodiment of the present invention.

FIG. 1 shows an assembly 10 provided at the proximal end of a borescope. The assembly 10 comprises a housing 12 and a handle portion 14 which can be grasped by a user's hand. An insertion tube (not shown) is connected to the distal end of the housing 12, shown on the left hand side in the figure.

The insertion tube contains a conventional visual system, that is a viewing window at the distal end, an objective lens system forming an image of an object and a relay system for transmitting the image to the proximal end of the insertion tube and into the housing 12 where the last relay lens 16 of the relay system is mounted.

An ocular lens 18 is provided towards the proximal end of the housing 12, shown on the right hand side in the figure. As is known in the art, the last relay lens 16 and ocular lens 18 may each be a single lens, or a combination of two or more lenses.

A focus collar 20 is rotatably mounted on the housing 12 and is described further below.

If the scope has a lateral direction of view, i.e. it views objects to the side of the insertion tube, it will contain a prism at the distal end of the insertion tube which inverts the image. To correct this inversion, a corrective system such as a dove prism 22 is provided, in this case, in the housing 12 proximal to the ocular lens 18. Furthermore, if the insertion tube is rotatable about its longitudinal axis to provide orbital scanning, a scan control collar 24 may be rotatably mounted on the housing 12.

Typically, illumination of an object being viewed is provided by a bundle of optical fibres transmitting light along the insertion tube from a light guide. In a conventional manner, a light guide connector 26 can be incorporated in the handle 14 coupling the optical fibre bundle (not shown) to a cable from an external light source (also not shown).

Thus, as in a conventional visual system, in the borescope of the present invention light from the relay lens 16 is passed to the ocular lens system 18, through the dove prism 22 for correction and then to an observer's eye positioned adjacent an eye piece at the proximal end of the assembly 10.

However, in addition, the present invention incorporates a beam splitter device 28 mounted between the last relay lens 16 and the ocular lens 18. This diverts a proportion of the light received from the last relay lens 16 substantially perpendicular to the optical path between the relay lens 16 and ocular lens 18, to an image-to-video conversion device such as a CCD 30 mounted at 90° to the optical path. The beam splitter device 28 may be of any type, although it is currently preferred for this to be a beam splitter cube, formed of two right-angled prisms with a coating on their interface plane.

A cable 32 connected to the handle portion 14 provides power input for, and receives a video output from, the CCD 30 for transmission to a display monitor (not shown). Thus, at the same time that an observer can directly view an image through the eyepiece, a video signal of the image can also be viewed on a display monitor.

Preferably, the system is designed to overfill the CCD 30, so as to give a full screen image on the display monitor. Also, to provide a clear defined edge to the image seen by an observer looking into the eyepiece, a field mask 34', i.e. a plate with a circular aperture, is placed at the location of the final real image of the system, between the last relay lens 16 and the beam splitter 28. The ocular lens 18 is designed to form a virtual image of both the field mask 34' and the final image at the same eye field of view as a conventional visual scope. FIG. 1 also shows field mask 34 located at a different location along the optical path.

Preferably, the CCD 30 is mounted on a support column 36, itself connected to a mounting carriage 38 which carries the ocular lens 18, field mask 34 and beam splitter 28. This carriage 38 is translatable in a direction parallel to the main optical path through the scope. This translation is achieved by the focus collar 20 which is coupled to the carriage 38 so that rotation of the focus collar 20 causes linear translation of the carriage 38. Thus, focussing can be achieved simultaneously for the CCD and the visible image paths for different working ranges of the scope. The lenses are designed such that the focus travel of both the CCD and ocular lens are the same for the required working range of specifications of the scope.

Furthermore, the optical design is such that spherical aberrations caused by the beam splitter device 28 are removed. A telecentric design is used such that the light rays from the last relay lens 16 are all parallel, in order to remove off axis aberrations such as astigmatism, coma and distortion that would otherwise be present when using a beam splitter device.

The image-to-video conversion device is a CCD board camera 30 which has a full digital signal processor (DSP) set. This means that the device is compact and only requires a power input and a video output cable 32. In the preferred embodiment, a power conversion board 40 is placed in the handle portion 14 such that a voltage range of 7–30 volts can be used as the input.

The CCD 30 is programmable to allow for correction of image inversion which occurs if an odd number of reflections appears in the system, as when the scope has a prism at the distal end for lateral viewing.

Alternatively, the beam splitter 28 can be configured so as to ensure an even number of reflections occur before light encounters the CCD 30, as shown in the second embodiment illustrated in FIG. 2. Here a first reflection occurs in the prism at the distal end of the insertion tube, and a second reflection in a dove prism 44 which is part of the relay lens system. Thus, light passing to ocular lens 18 has undergone two reflections. The beam splitter 28 is arranged to provide two further reflections to ensure that the CCD receives an even number of image reflections.

Typically, the beam splitter 28 will be configured to transmit approximately 50% of light it receives through to the ocular lens 18, and to divert the other 50% of the light towards the CCD 30. However, it is anticipated that future CCD sensors may become more sensitive and if so the ratio can be altered to maximise the image brightness for both the visual and video systems.

Furthermore, in certain applications it may be preferable to maximise the light throughput either through the visual or video systems. In a third embodiment of the invention illustrated in FIG. 3, an additional device 46 is provided which provides three alternative elements, mounted side by side. In the centre is a beam splitter cube 28, which transmits a portion of light received from the relay lens 16 on to the ocular lens 18 and diverts the remaining portion to the CCD. On one side, an element 48 such as a glass cube transmits all the light and diverts none. On the other side, a third element 50, such as a prism, diverts all the light to the CCD 30 and transmits none to the ocular lens 18. The dimensions of these elements 28, 48, 50 are such that the optical path length to the final image remains the same. The device 46 can then be moved in a direction perpendicular to the optical path, as indicated by the arrows, such that a user may select which element 28, 48, 50 is placed in the optical path and thus whether all the light is diverted to the CCD 30, or all the light is passed to the eye, or whether there is a split between the two.

Thus, the present invention provides a borescope with combined visual and video capability in a single compact arrangement. The benefits of both visual and video systems are available simultaneously. The skilled reader will appreciate that a number of alterations and modifications may be made to the precise details prescribed, without departing from the scope of the invention as set out in the claims.

The invention claimed is:

1. An assembly for a borescope, comprising a body having a distal end for connection to an insertion tube and a proximal end providing an eyepiece into which an observer may look, the body containing a relay lens for receiving light from a relay system in the insertion tube, an ocular lens for creating a virtual image for viewing by an observer and a beam splitter device mounted in the optical path between the relay lens and the ocular lens and operable to divert a proportion of light received from the relay lens to an image-to-video conversion device mounted laterally to the optical path, and wherein the ocular lens, beam splitting device and image-to-video conversion device are located in a common mounting translatable in a direction parallel to the optical path to allow for focusing, and wherein said common mounting is supported by said body and translatable relative to said body.

2. An assembly as claimed in claim 1, further comprising a collar rotatably mounted on the body and coupled to the common mounting such that rotation of the collar causes translation of the mounting in a direction parallel to the optical path.

3. An assembly as claimed in claim 1, wherein the beam splitter device is a beam splitter cube operable to divert a proportion of light at substantially 90° to the optical path.

4. An assembly as claimed in claim 1, wherein the beam splitter device is operable to divert approximately 50% of light received to the image-to-video conversion device.

5. An assembly as claimed in claim 1, wherein the beam splitter device is adjustable to alter the proportion of light diverted to the image-to-video conversion device.

6. An assembly as claimed in claim 1, wherein the beam splitter device comprises a first element operable to transit all light received from the relay lens along the optical path to the ocular lens, a second element operable to transmit a first proportion of light along the optical path and to divert a second proportion of light to the image-to-video conversion device and a third element operable to divert all the light received to the image-to-video diversion device, wherein the first, second and third elements are selectively moveable to position one element at a time in the optical path.

7. An assembly as claimed in claim 1, wherein the image-to-video conversion device comprises a CCD board camera.

8. An assembly as claimed in claim 7, wherein the CCD board camera comprises a full digital signal processing means.

9. An assembly as claimed in claim 1, wherein the image-to-video conversion device is programmable to allow for correction of image inversion.

10. An assembly as claimed in claim 1, wherein the beam splitter device is configured to ensure an image received by the image-to-video conversion device has been reflected an even number of times.

11. An assembly as claimed in claim 1, further comprising an inversion correction device mounted in the body proximal to the ocular lens.

12. An assembly as claimed in claim 1, further comprising a field mask mounted in the optical path between the relay lens and the beam splitter device.

13. A borescope comprising an insertion tube connected to an assembly as claimed in claim 1.

14. An assembly as claimed in claim 1, wherein the ocular lens and the image-to-video conversion device are mounted on said common mounting in a manner which results in simultaneous focusing upon adjustment of said common mounting.

* * * * *